US011026603B2

(12) United States Patent
Omenetto et al.

(10) Patent No.: US 11,026,603 B2
(45) Date of Patent: Jun. 8, 2021

(54) SYSTEM AND METHOD OF USING A TOOTH ANTENNA

(71) Applicant: Trustees of Tufts College, Medford, MA (US)

(72) Inventors: Fiorenzo G. Omenetto, Lexington, MA (US); Peter Tseng, Saratoga, CA (US); Bradley Napier, Madison, CT (US); Mark Brenckle, Acton, MA (US); Logan Garbarini, Boulder, CO (US)

(73) Assignee: Trustees of Tufts College, Medford, MA (US)

( * ) Notice: Subject to any disclaimer, the term of this patent is extended or adjusted under 35 U.S.C. 154(b) by 218 days.

(21) Appl. No.: 16/374,496

(22) Filed: Apr. 3, 2019

(65) Prior Publication Data

US 2019/0298234 A1 Oct. 3, 2019

Related U.S. Application Data

(60) Provisional application No. 62/652,192, filed on Apr. 3, 2018.

(51) Int. Cl.
*A61B 5/145* (2006.01)
*G01N 27/02* (2006.01)
*A61B 5/1468* (2006.01)
*A61B 5/00* (2006.01)

(52) U.S. Cl.
CPC ........ *A61B 5/14507* (2013.01); *A61B 5/1468* (2013.01); *A61B 5/14532* (2013.01); *A61B 5/14539* (2013.01); *A61B 5/14546* (2013.01); *A61B 5/682* (2013.01); *G01N 27/028* (2013.01); *A61B 5/4845* (2013.01)

(58) Field of Classification Search
CPC ......... A61B 5/145; A61B 5/00; A61B 5/1468; A61B 5/14532; A61B 5/14507; A61B 5/14546; A61B 5/682; A61B 5/14539; A61B 5/146; A61B 5/4845; A61B 5/01; G01N 27/02; G01N 27/028
See application file for complete search history.

(56) References Cited

PUBLICATIONS

Ekmekci, Evren & Turhan-Sayan, Gonul. (2011). Metamaterial sensor applications based on broadside-coupled SRR and V-Shaped resonator structures. IEEE Antennas and Propagation Society, AP-S International Symposium (Digest). 1170-1172. 10.1109/APS.2011. 5996492. (Year: 2011).*

Bandodkar, A. J., et al. "Epidermal tattoo potentionmetric sodium sensors with wireless signal transduction for continuous non-invasive sweat monitoring." Biosensors and bioelectronics 54 (2014): 603-609.

Brenckle, M. A., et al. "Protein-Protein Nanoimprinting of Silk Fibroin Films." Advanced materials 25.17 (2013): 2409-2414.

(Continued)

*Primary Examiner* — Eric J Messersmith
(74) *Attorney, Agent, or Firm* — Quarles & Brady, LLP

(57) ABSTRACT

This disclosure provides a dielectric sensor configured to detect a physiological variable within a subject. The dielectric sensor having at least one split-ring resonator configured to be positioned within an oral cavity of the subject and to be bioresponsive to at least one physiological variable. The split-ring resonator having a first resonator loop, a second resonator loop, and a dielectric interlayer interposed between and contacting the first resonator and the second resonator.

18 Claims, 6 Drawing Sheets

(56) References Cited

PUBLICATIONS

Chen, L. Y., et al. "Continuous wireless pressure monitoring and mapping with ultra-small passive sensors for health monitoring and critical care." Nature communications 5 (2014): 5028.

Chen, X., et al. "Conformation transition kinetics of Bombyx mori silk protein." Proteins: Structure, Function, and Bioinformatics 68.1 (2007): 223-231.

Ekmekci, E., et al. "Frequency tunable terahertz metamaterials using broadside coupled split-ring resonators." Physical Review B 83.19 (2011): 193103.

Gao, W., et al. "Fully integrated wearable sensor arrays for multiplexed in situ perspiration analysis." Nature 529.7587 (2016): 509.

Gao, X., et al. "pH-and thermo-responsive poly(N-isopropylacrylamide-co-acrylic acid derivative) copolymers and hydrogels with LCST dependent on pH and alkyl side groups." Journal of Materials Chemistry B 1.41 (2013): 5578-5587.

Hoare, T. et al. "Highly pH and temperature responsive microgels functionalized with vinylacetic acid." Macromolecules 37.7 (2004): 2544-2550.

Kim, J., et al. "Non-invasive mouthguard biosensor for continuous salivary monitoring of metabolites." Analyst 139.7 (2014): 1632-1636.

Kim, J., et al. "Wearable salivary uric acid mouthguard biosensor with integrated wireless electronics." Biosensors and Bioelectronics 74 (2015): 1061-1068.

Lee, H.-J., et al. "A planar split-ring resonator-based microwave biosensor for label-free detection of biomolecules." Sensors and Actuators B: Chemical 169 (2012): 26-31.

Lee, H.-J., et al. "Biosensing using split-ring resonators at microwave regime." Applied Physics Letters 92.25 (2008): 254103.

Lee, H.-J., et al. "DNA sensing using split-ring resonator alone at microwave regime." Journal of Applied Physics 108.1 (2010): 014908.

Partlow, B. P., et al. "Highly tunable elastomeric silk biomaterials." Advanced functional materials 24.29 (2014): 4615-4624.

Rockwood, D. N., et al. "Materials fabrication from Bombyx mori silk fibroin." Nature protocols 6.10 (2011): 1612.

Roychoudhury, S., et al. "Recent advances in metamaterial split-ring-resonator circuits as biosensors and therapeutic agents." Biosensors and Bioelectronics 86 (2016): 595-608.

Tao, H., et al. "Silk-based conformal, adhesive, edible food sensors." Advanced Materials 24.8 (2012): 1067-1072.

Tseng, P., et al. "Directed assembly of bio-inspired hierarchical materials with controlled nanofibrillar architectures." Nature nanotechnology 12.5 (2017): 474.

Windmiller, J.R. et al. "Wearable electrochemical sensors and biosensors: a review." Electroanalysis 25.1 (2013): 29-46.

Zhang, J., et al. "Dual thermo-and pH-sensitive poly(N-isopropylacrylamide-co-acrylic acid) hydrogels with rapid response behaviors." Polymer 48.6 (2007): 1718-1728.

* cited by examiner

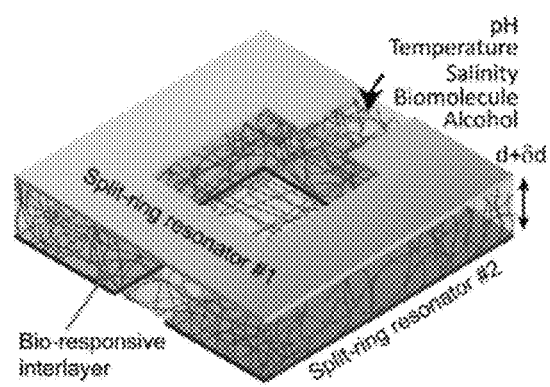
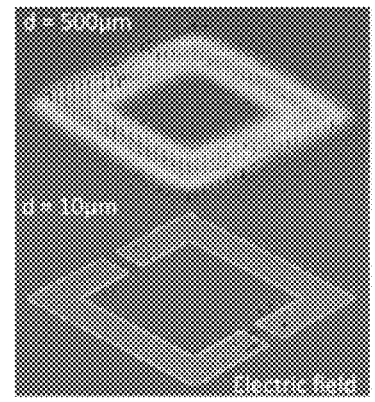
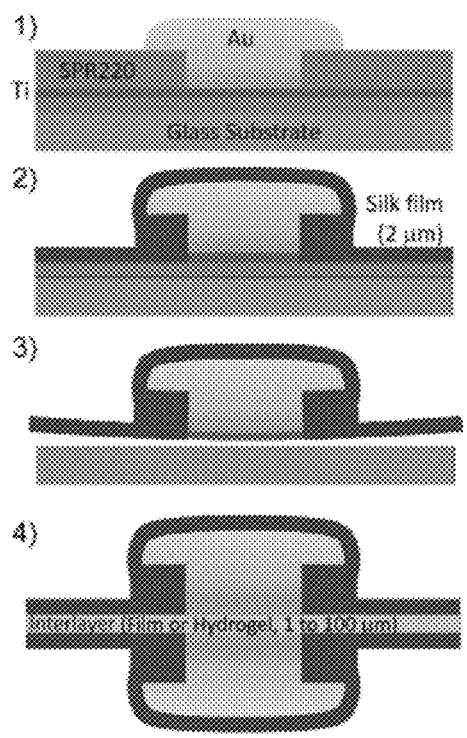
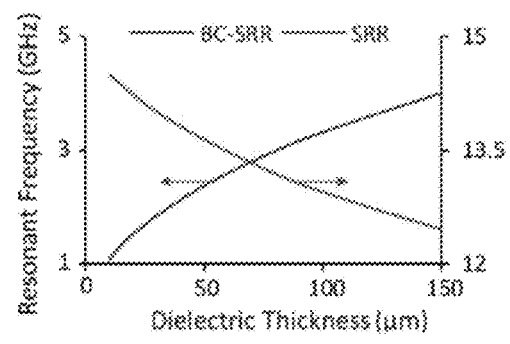
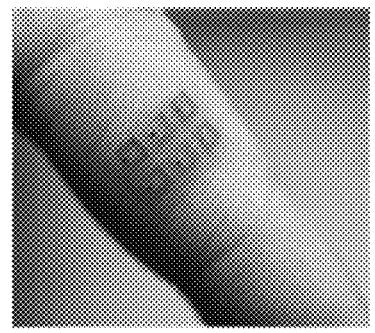
FIGS. 3A-E

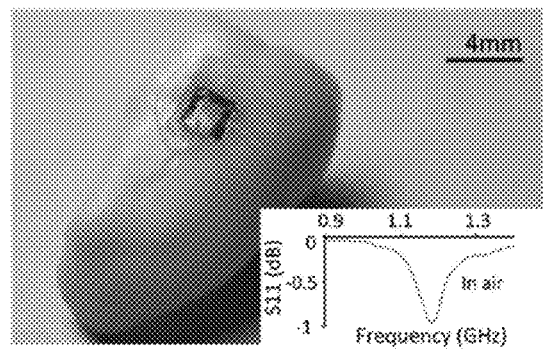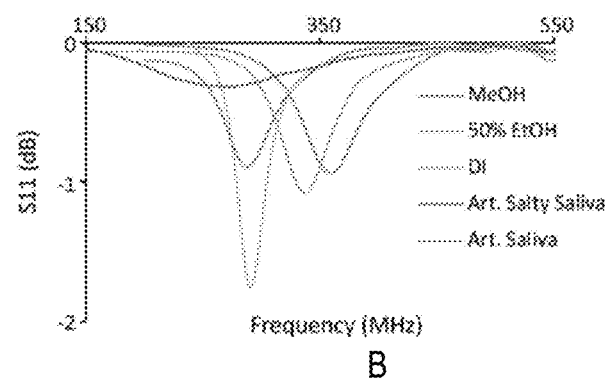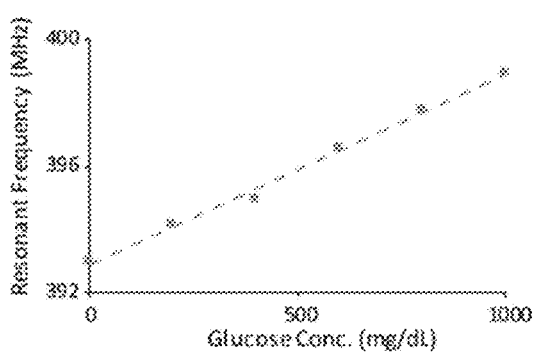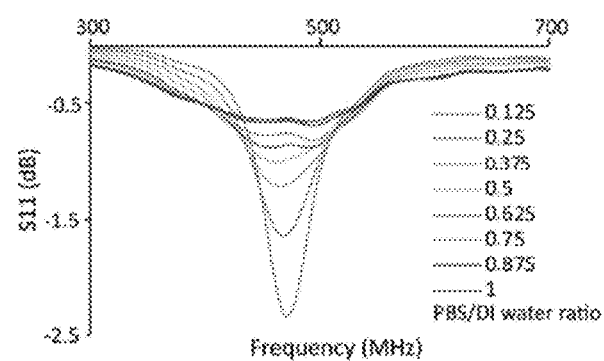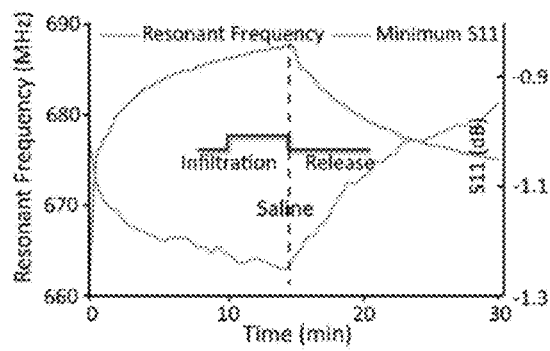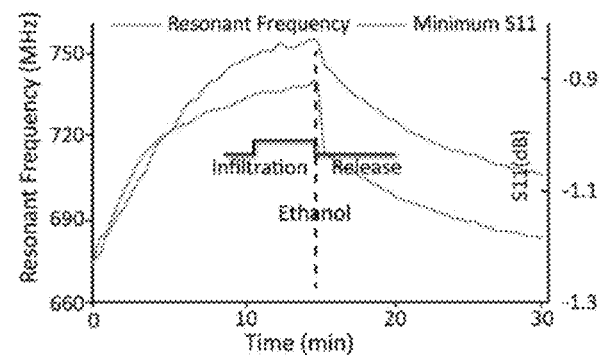
FIGS. 4A-F

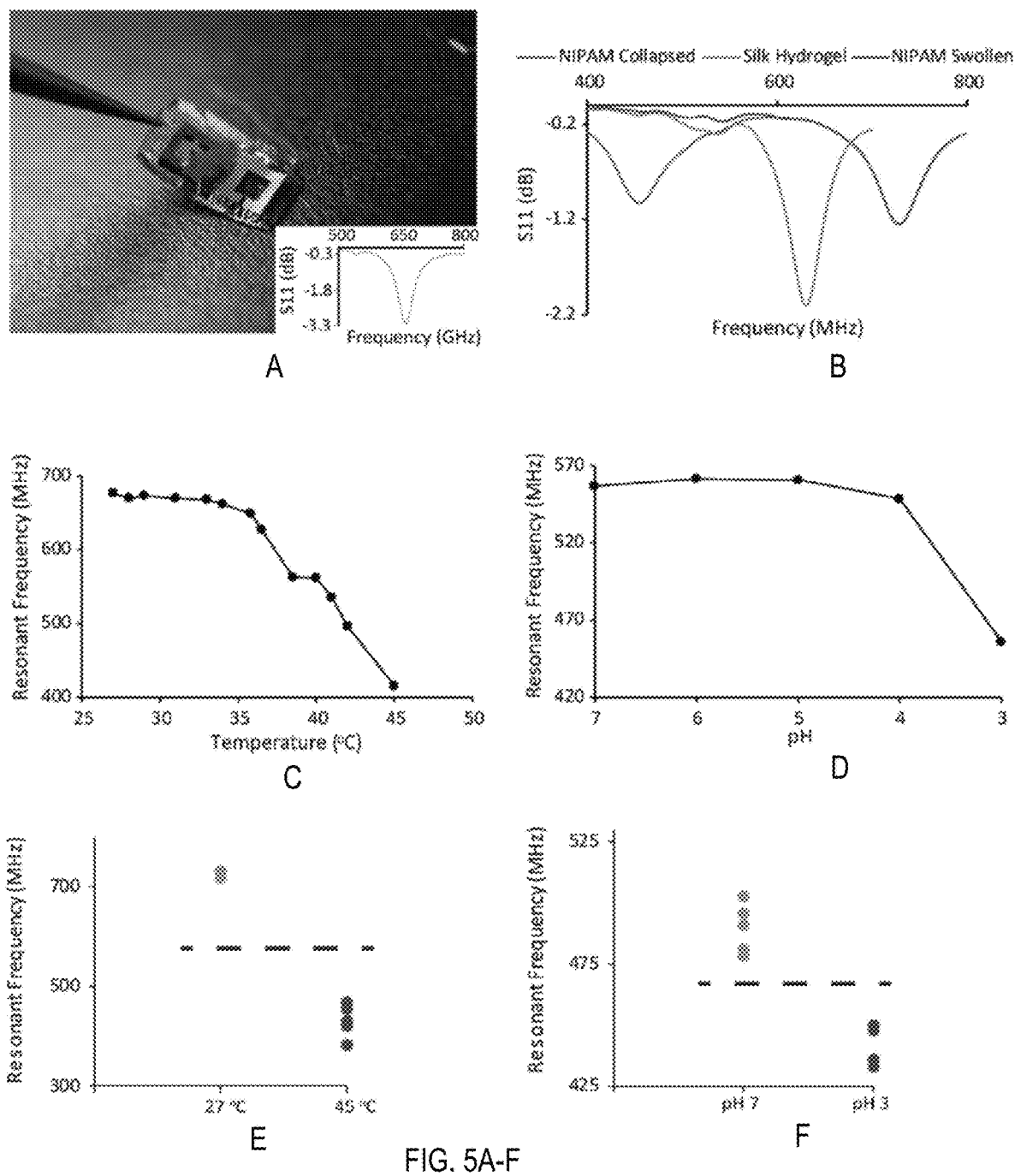
FIG. 5A-F

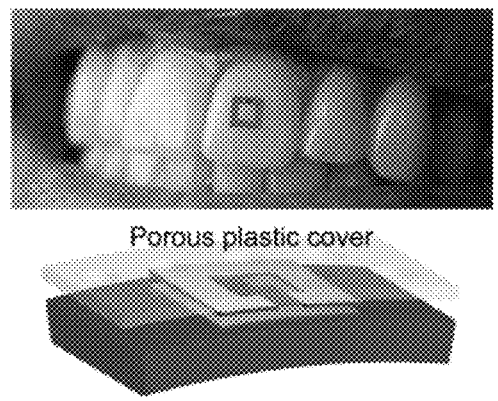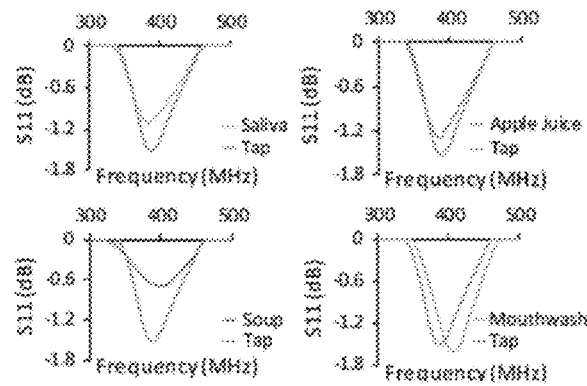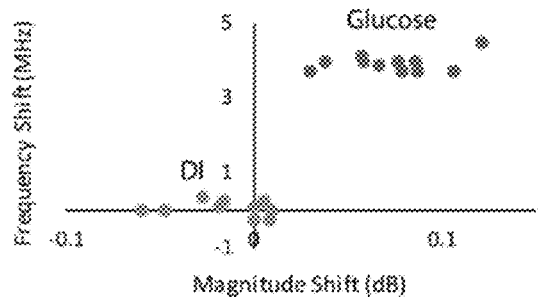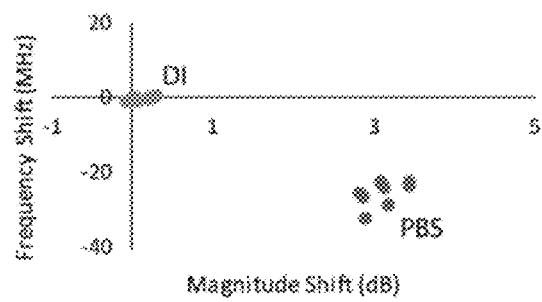
FIG. 6A-D

SYSTEM AND METHOD OF USING A TOOTH ANTENNA

CROSS-REFERENCE TO RELATED APPLICATIONS

This application is based on, incorporates herein by reference, and claims the benefit of U.S. Provisional Patent Application No. 62/652,192, filed Apr. 3, 2018, and entitled "SYSTEM AND METHOD OF USING A TOOTH ANTENNA".

STATEMENT REGARDING FEDERALLY SPONSORED RESEARCH

This invention was made with government support under grant numbers W911QY-15-2-0001 awarded by the United States Army, EB021159 awarded by the National Institutes of Health, and N00014-13-1-0596 awarded by the United States Navy. The government has certain rights in the invention.

BACKGROUND

1. Field of the Invention

This invention relates to biological sensors. More specifically, this invention relates to dielectric sensors for measuring physiological variables in an oral cavity of a subject.

2. Description of the Related Art

Noninvasive medical devices are quickly emerging as powerful tools to provide data to assess individual health and wellness. In this context, conformal interfaces in the form of flexible devices and tattoos have emerged demonstrating measurement of physiological variables such as electricity, pressure, and/or analyte sensing among others. In contrast to traditional, wearable devices that require mechanical fixation, such devices possess a low form factor and conform to surfaces, minimizing user impact while ensuring maximum proximity to the biological surface to be measured. Such sensors find use for monitoring of physiological parameters (such as glucose levels, hydration, and heartrate, to name a few) and can be applied in constrained environments.

Few accurate, low user burden methods exist for self-assessment of both intake and corresponding physiological responses to diet and nutrition. In situ sensing of food consumption could potentially provide conclusive links between dietary intake and health. In order to directly access the oral cavity, several devices have been investigated, in particular mouthguard-based electrochemical sensors or tooth tattoos. The form factor and wiring requirements of electrochemical sensors prevent facile integration of these sensors into the mouth without a mechanical support (i.e., a mouthguard). While radiofrequency (RF)-sensing provides a more elegant solution, it comes with drawbacks such as dimensional challenges that can limit its in vivo applications.

Conformal sensors typically rely on either dielectric or electrochemical sensing methodologies. Dielectric sensors probe an analyte (typically a biofluid) through its impedance spectrum, and can be configured for wireless sensing via radio waves. Such sensors are easily fabricated in flexible, compact epidermal formats and can utilize existing radiofrequency identification (RFID) infrastructure for data readout. Typical drawbacks for these systems are the size imposed by the selected RF operational band, measurement inconsistency, motion artifacts, and lower sensitivity to relevant biosignals such as sugars or pH. Electrochemical sensors rely on redox reactions occurring between an activated electrode surface and the analyte thus offering greater sensitivity than dielectric sensors at the expense of requiring a direct electrical connection to often bulky electrical measurement equipment that can significantly increase the device footprint even in mobile formats. Furthermore, these devices are typically more expensive to fabricate (requiring immobilization of enzymes and biomolecules), possess a short operation window (several days due to inherent biofouling or enzyme degradation), and often require carbonaceous materials that have undetermined biocompatibility.

Thus, there is a need for improved low form factor medical systems and methods for providing in situ for monitoring of physiological parameters.

SUMMARY

The present disclosure addresses the aforementioned shortcomings by providing systems and methods that utilize a compact bio-sensing dielectric devices on the millimeter-scale, thus extending the practical adoptability of such sensors. In one aspect, the sensors are sized and designed to fit onto a single human tooth to sample biofluids in the oral cavity and discriminate between physiological parameters, such as the concentration of consumed foods or liquids. The favorable functionality and reduced form factor of the dielectric sensor may be achieved through the use of a split-ring resonator and unique material selections.

In one aspect, the present disclosure provides a dielectric sensor configured to detect a physiological variable within a subject. The dielectric sensor may comprise at least one split-ring resonator configured to be positioned within an oral cavity of the subject and to be bioresponsive to at least one physiological variable. The split-ring resonator may comprise a first resonator loop, a second resonator loop arranged in a split-ring resonator formation with the first resonator loop, and a dielectric interlayer interposed between and contacting the first resonator and the second resonator.

In another aspect, the present disclosure provides a bio-sensing system configured to detect a physiological variable within a subject. The bio-sensing system may comprise at least one split-ring resonator configured to be positioned within an oral cavity of the subject and to be bioresponsive to at least one physiological variable. The split-ring resonator may comprise a first resonator loop, a second resonator loop arranged in a split-ring resonator formation with the first resonator loop, and a dielectric interlayer interposed between and contacting the first resonator and the second resonator. The bio-sensing system may further comprise a radiofrequency (RF) network analyzer configured to detect the resonant frequency and amplitude generated by the at least one split-ring resonator, and a processing system coupled to the RF network analyzer. The processing system may be configured to control the RF network analyzer to detect the resonant frequency and amplitude generated by the at least one split-ring resonator, and provide information regarding the at least one physiological variable.

In yet another aspect, the present disclosure provides a method of detecting a physiological variable within a subject. The method may comprise positioning a dielectric sensor within an oral cavity of the subject, wherein the dielectric sensor comprises at least one split-ring resonator configured to be bioresponsive to at least one physiological variable. The method may further comprise applying a controlled electromagnetic field to the dielectric sensor, detecting the resonant frequency and amplitude generated by the dielectric sensor, and providing information regarding the at least one physiological variable.

These and other features, aspects, and advantages of the present invention will become better understood upon consideration of the following detailed description, drawings, and appended claims.

BRIEF DESCRIPTION OF THE DRAWINGS

FIGS. 3A-E depict experimental RF-trilayer sensors configurations, images, and graphical results of the experiment of Example 1. FIG. 3A: schematic of broad-side coupled split-ring resonators with an interlayer of silk film or responsive hydrogel. Interlayers swell and absorb surrounding solvent (changing thickness and dielectric constant) and result in a change in resonant frequency and amplitude of the sensor. FIG. 3B: simulation (COMSOL Multiphysics) of the electric field of a 1 mm thick interlayer. Field lines focus within the structure and at the split-ring. Reducing interlayer thickness lead to increasing dominance of the interlayer capacitance as opposed to the split ring in the construct's resonant frequency.

FIG. 3C: abbreviated fabrication protocol. Split-ring resonators integrated into a silk film are used as the base for functional interlayers. FIG. 3D: simulated resonant frequency of trilayer sensors in air with different thicknesses of interlayer (permittivity: 4). FIG. 3E: 2 mm dielectric sensor array applied to a human finger.

FIGS. 4A-F depict in vitro performance results of the experimental biopolymer film-based sensors of Example 1. FIG. 4A: 2 mm by 2 mm trilayer sensor conforming around a human tooth. Inset: Resonant response of the sensor when dry. FIG. 4B: base response of a single thin interlayer ($\approx$1.2 µm) sensor to various solvents and solutions. FIG. 4C: changing resonant frequency of a thin interlayer sensor as a function of glucose concentration. FIG. 4D: resonant response of a thin interlayer sensor as a function of salinity. FIGS. 4E-F: sensor temporal response of the same thick interlayer sensor ($\approx$2.3 µm) to infiltration and release of high salinity and high alcohol concentrations.

FIGS. 5A-F depict experimental results for the development of responsive hydrogel-interlayer sensors of Example 1. FIG. 5A: Image of silk hydrogel-interlayer structure. FIG. 5B: Comparison of spectral response from silk hydrogel and PNIPAM hydrogel (collapsed due to temperature and native swollen state). FIG. 5C: Initial shift in resonant frequency of a PNIPAM interlayer sensor as a function of temperature. FIG. 5D: Initial shift in resonant frequency of a PNIPAM interlayer sensor as a function of pH. FIG. 5E: Measured resonant frequency shifts of the sensor as a function of operational cycles when the temperature is cycled between 27 and 45° C. change in temperature. FIG. 5F: measured resonant frequency shifts of the sensor as a function of repeated pH changes.

FIGS. 6A-D depict experimental image and graphical results for the experiment of Example 1. FIG. 6A: trilayer sensor adhered to a human subject's tooth for in vivo monitoring of ingested fluids. FIG. 6B: thin interlayer ($\approx$1.2 µm) response on Subject 1 to various liquids. Changes to frequency and magnitude are seen in each case. FIG. 6C: evaluation of benchtop response of sensor exposed to multiple repeated solution changes between DI and glucose (0.5 g dL$^{-1}$), and between DI and PBS (FIG. 6D). Magnitude and frequency shift of the resonant peak are plotted. The data show acceptable repeatability in the frequency response to both solutions over one week of data collection.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Features of this disclosure described with respect to a particular method, apparatus, composition, or other aspect of the disclosure can be combined with, substituted for, integrated into, or in any other way utilized with other methods, apparatuses, compositions, or other aspects of the disclosure, unless explicitly indicated otherwise or necessitated by the context. For clarity, an aspect of the invention described with respect to one method can be utilized in other methods described herein, or in apparatuses or with compositions described herein, unless context clearly dictates otherwise.

The present disclosure provides novel biological sensing systems and methods that allow for the sampling of fluids in the oral cavity of a subject in order to evaluate a physiological variable.

Figure 1A:
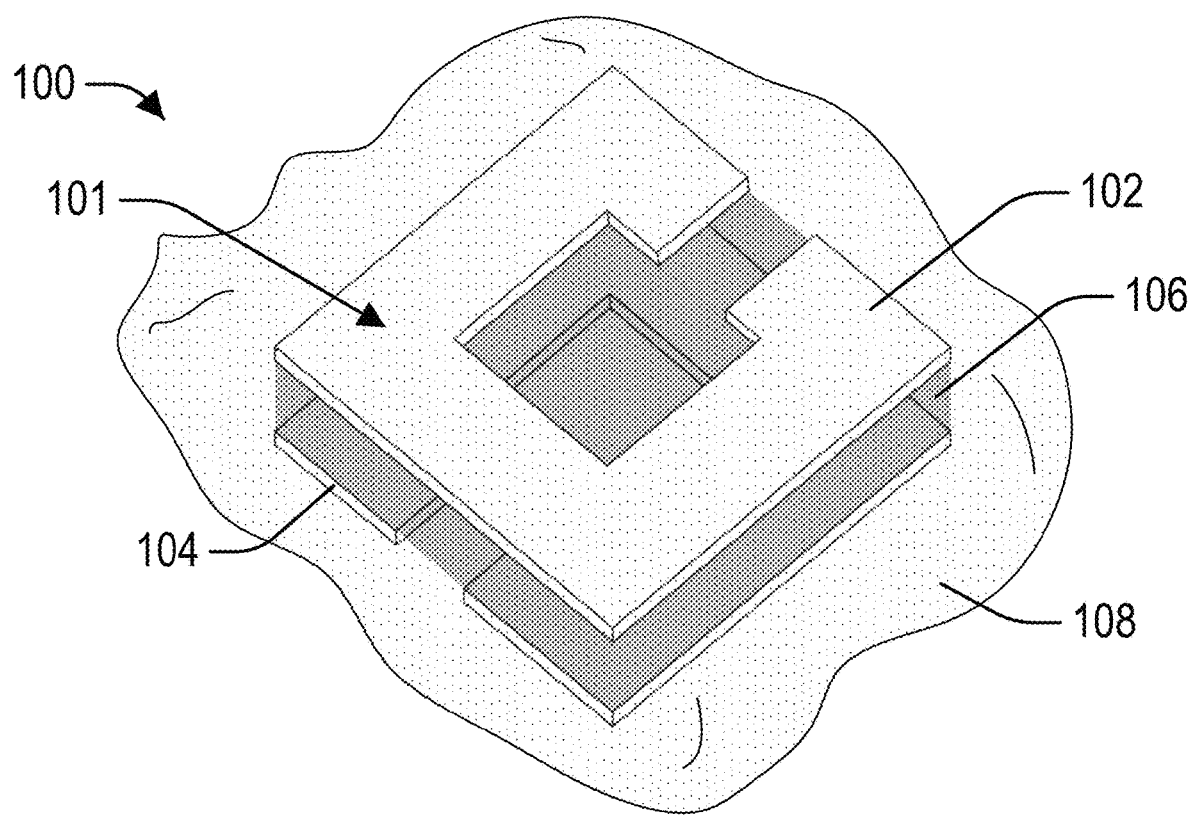
FIG. 1A is a schematic depiction of a dielectric sensor, in accordance with one aspect of the present disclosure. For clarity between the multiple layers, various components have been shaded or patterned.

Referring to FIG. 1A, a dielectric sensor 100 configured to detect a physiological variable within a subject is depicted. The dielectric sensor 100 may comprise a split-ring resonator 101 configured to be positioned within an oral cavity of the subject and to be bioresponsive to at least one physiological variable. The split-ring resonator may comprise a first resonator loop 102 and a second resonator loop 104 arranged in a split-ring resonator formation with the first resonator loop 101. The dielectric sensor 100 may also comprise a dielectric interlayer 106 interposed between and contacting the first resonator 102 and the second resonator 104. In one version, the dielectric sensor 100 may have an outer layer 108 which envelops the split-ring resonator 101.

The first resonator loop 102 and the second resonator loop 104 may be generally formed of metallic films having a split. For instance, the first resonator loop 102 and the second resonator loop 104 may be formed of gold, copper, or a comparable material. The split of the first resonator loop 102 may be positioned in a complementary manner to the split of the second resonator loop 104. The first resonator loop 102 and the second resonator loop 104 may be arranged in a variety of split-ring resonator geometries. For instance, the split-ring resonator 101 may have a complementary, broadside-coupled, edge-coupled complementary, or broadside couple complementary formation. The dielectric sensor 100 may specifically have a broadside-coupled arrangement, which can allow for increased sensitivity by concentrating of the E-field between the two resonator loops. In another form, the dielectric sensor 100 may have only a single resonator loop that functions as the split-ring resonator.

The dielectric interlayer 106 may be configured to be bioresponsive to at least one physiological variable. Thus, at least one property of the dielectric interlayer may undergo a change in response to a change in the physiological variable. The dielectric interlayer 106 may undergo a change in thickness as the bioresponse to the at least one physiological variable. Alternatively, the overall dielectric constant of the dielectric interlayer 106 and any contained fluids or analytes may undergo a change as the bioresponse to the at least one physiological variable. The physiological variable may be selected from the group consisting of glucose concentration, ethanol concentration, salinity, pH, and temperatures. For instance, an increase in concentration of a specific analyte may lead to an increase or decrease in the overall dielectric constant of the dielectric interlayer 106. Additional physiological variables of interest that are commonly associated with the oral cavity may also be monitored. The bioresponsive changes may in turn lead to a measurable change in the resonant frequency and amplitude of the dielectric sensor 100. By monitoring the resonant frequency and amplitude, the presence and degree or concentration of the physiological variable can be determined.

The dielectric interlayer 106 may be positioned between the first resonator loop 102 and the second resonator loop 104 so that it contacts both loops. The dielectric interlayer 106 may encompass the entire space between the first resonator loop 102 and the second resonator loop 104. The dielectric interlayer 106 may comprise a material selected from the group consisting of a silk film, a silk gel, a responsive poly(N-isopropylacrylamide) hydrogel, a PNIPAM-based hydrogel, and combinations thereof. The dielectric interlayer thickness 106 between the first resonator loop 102 and the second resonator loop 104 may be between 0.5 and 3 micrometers, between 0.5 and 2 micrometers, or about 1 micrometer.

The dielectric sensor 100 may be particularly suited for and configured to be positioned within an oral cavity of a subject. The unique material selections and design allow the dielectric sensor to have a compact design. For instance, the dielectric sensor may be sized to fit within a 5 mm by 5 mm by 3 mm box, within a 3 mm by 3 mm by 1 mm box, or within a 2 mm by 2 mm by 0.5 mm box. The dielectric sensor may be biocompatible, and may also be configured to resist degradation in the environment of an oral cavity. The dielectric sensor may be configured to be flexible enough to contour to a curved edge without breaking or losing functionality.

Figure 1B:
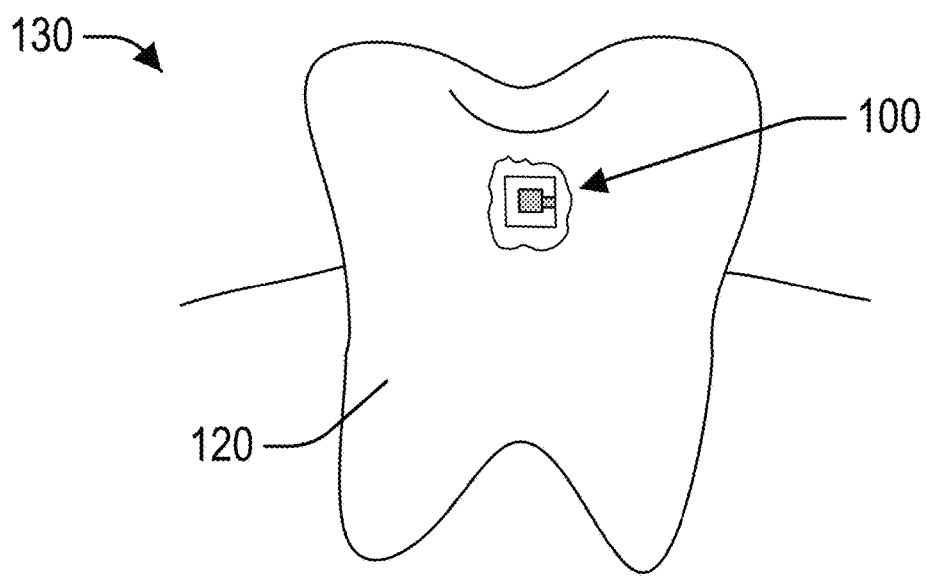
FIG. 1B is a schematic depiction of the dielectric sensor of FIG. 1A integrated with a tooth, in accordance with one aspect of the present disclosure. For clarity between the multiple layers, various components have been shaded or patterned.

As shown in FIG. 1B, the dielectric sensor 100 may be configured to integrate with a tooth 120 in an oral cavity 130 of a subject. To achieve this functionality, the dielectric sensor may be sized or shaped to remain integrated with a tooth of a subject. The dielectric sensor may be adhesively attached to the tooth. Alternatively, the dielectric sensor may be positioned within a recess or cavity of the tooth. The dielectric sensor may include additional components such as an exterior adhesive or porous cover to assist in maintaining integration with the tooth. The porous outer layer 108 may envelope split-ring resonator and may serve to protect the individual resonator loops and dielectric interlayer from direct exposure to the environment of the dielectric sensor. The porous outer layer 108 may comprise silk fibroin.

In another aspect, a method of making the dielectric sensor described herein is provided. The method may comprise arranging the first resonator loop, the second resonator loop, and the dielectric interlayer to form the dielectric sensor described herein. The method may further comprise calibrating the dielectric sensor to account for variabilities in positioning, composition, and thicknesses.

In one aspect, a bio-sensing system configured to detect a physiological variable within a subject is provided. The bio-sensing system may comprise at least one split-ring resonator configured to be positioned within an oral cavity of the subject and to be bioresponsive to at least one physiological variable. The split-ring resonator of the dielectric sensor described herein may be used. Thus, the split-ring resonator may have a first resonator loop, a second resonator loop arranged in a split-ring resonator formation with the first resonator loop, and a dielectric interlayer interposed between and contacting the first resonator and the second resonator. The split-ring resonator of the bio-sensing system may have any of the properties or configurations described herein for the dielectric sensor.

The bio-sensing system may further comprise a radiofrequency (RF) network analyzer configured to detect the resonant frequency and amplitude generated by the at least one split-ring resonator, and a processing system coupled to the RF network analyzer. The processing system may be configured to control the RF network analyzer to detect the resonant frequency and amplitude generated by the at least one split-ring resonator, and provide information regarding the at least one physiological variable. The processing system may be configured to control the RF network analyzer to apply a controlled electromagnetic field to the dielectric sensor. In one version, the processing system of the bio-sensing system may be located within the oral cavity. Alternatively, the processing system may be positioned externally.

The processing system may detect and provide information regarding the at least one physiological variable continuously, periodically, or only actively on demand. The processing system may utilize a mobile phone or tablet device when detecting and providing the information. One of skill in the art would readily envision additional alternative configurations and instrumentation for the components of the processing system.

The information regarding the at least one physiological variable may be used to provide an alert to a user. For instance, the physiological variable may be glucose concentration, and the bio-sensing system may provide an alert to either the subject or a physician if a high concentration is detected or if a concentration threshold is exceeded multiple times in a given period of time. In this manner, dietary behavior of the subject may be directly monitored for either personal use or clinical control. As another instance, a subject who has recently undergone an oral procedure may be monitored to ensure that a concentration of a physiological variable indicative of oral health is within an acceptable range, and provide an alert if the concentration falls out of range. As another application, the bio-sensing system may be used to detect a physiological variable that is indicative of a disorder or illness. For instance, the physiological variable may be the concentration of a specific saliva protein that is known to be correlated with a cardiovascular disease. As yet another application, the bio-sensing system may be used in tandem with an ignition interlock device in order to rapidly detect the presence of ethanol in the oral cavity of the subject. Unlike traditional car breathalyzer systems, because the dielectric sensor would be directly integrated with the subject, this would prevent the subject from bypassing the ignition interlock device by using compressed air or the breath of a companion.

The split-ring resonators of the present disclosure may have functionalized dielectric interlayers that are tailored to undergoing a change in the presence of a specific analyte or analyte grouping. The dielectric sensor and bio-sensor system described herein may be used to detect multiple physiological signals. The multiple physiological signals may be detected using a single split-ring resonator. Alternatively, the dielectric sensor and bio-sensor system may comprise multiple, multiplexed split-ring resonators. The multiple split ring resonators may have different sizes, shapes, dielectric interlayer compositions, dielectric interlayer thicknesses, or resonator loop compositions.

Figure 2:
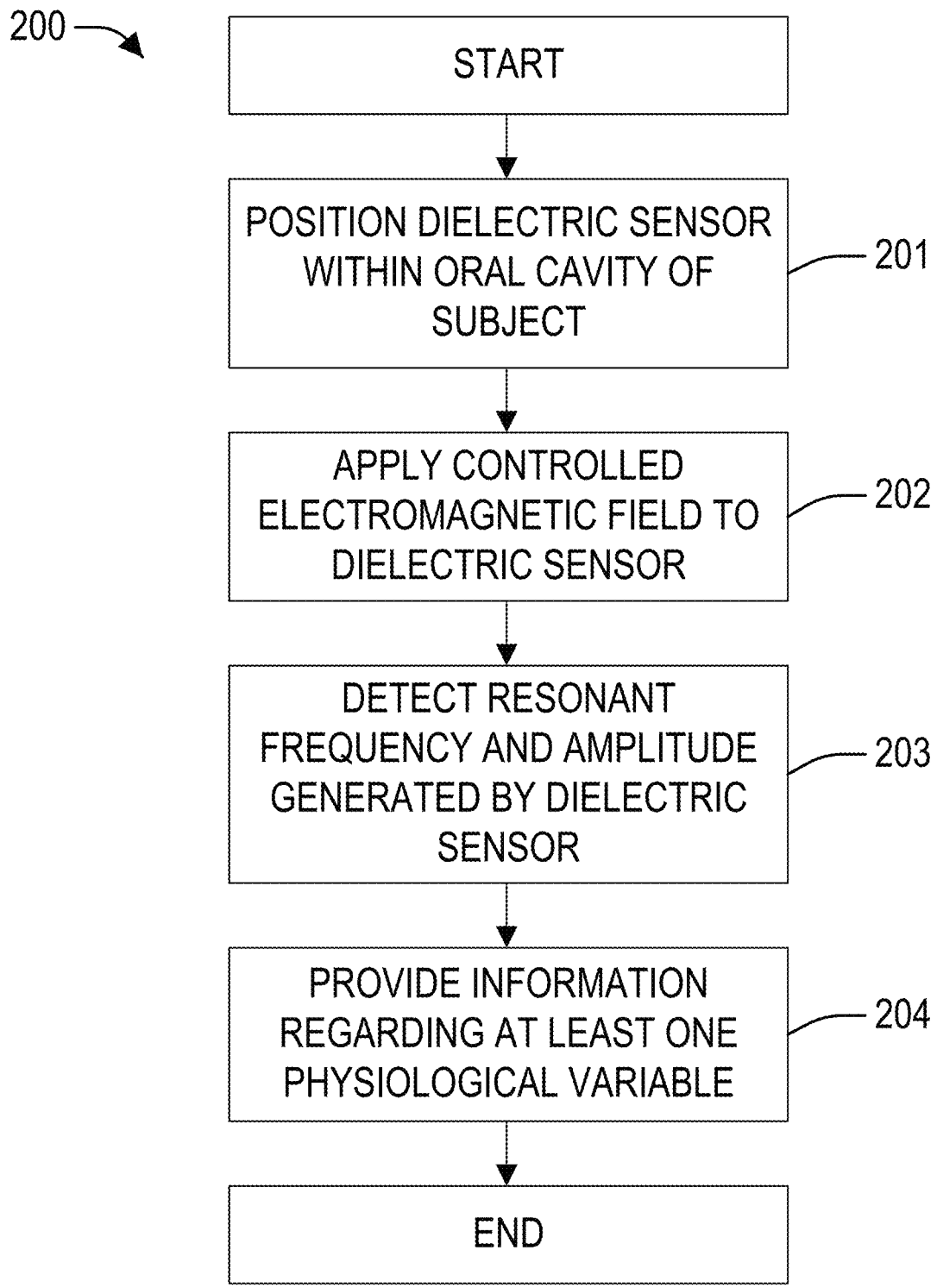
FIG. 2 is a process flowchart for a method of detecting a physiological variable within a subject, in accordance with one aspect of the disclosure.

Referring to FIG. 2, a method 200 of detecting a physiological variable within a subject is provided. The method may comprise positioning a dielectric sensor within an oral cavity of the subject 201, wherein the dielectric sensor comprises at least one split-ring resonator configured to be bioresponsive to at least one physiological variable. The method may also comprise applying a controlled electromagnetic field to the dielectric sensor 202, detecting the resonant frequency and amplitude generated by the dielectric sensor 203, and providing information regarding the at least one physiological variable 204. The method may include any of the configurations, applications, and techniques described herein for the dielectric sensor and biosensor system.

EXAMPLES

The following Example is provided in order to demonstrate and further illustrate certain embodiments and aspects of the present disclosure and are not to be construed as limiting the scope of the disclosure.

Example 1

In order to adequately test the systems and methods of the present disclosure, experiments were conducted using synthesized dielectric sensors.

A metamaterial-based approach was adopted by using a broadside-coupled, split ring resonator (BC-SRR) geometry (composed of two stacked, reverse facing SRRs) into a flexible format. BC-SRR geometries are favorable because of their combined small form factor and lower resonant frequency that make the devices practical for use with traditional RF instrumentation. In addition, the electric field is localized between the two resonators limiting the influence of the external environment on the device response. The sensor can conform to curved surfaces, such as the human tooth, and for this application the curvature of the sensor does not change during use. However, if applied to more dynamic surfaces, the effect of sensor bending on the resonant frequency during use (such as mechanical compression of the interlayer) can be taken into account and the materials and interfaces optimized for this purpose.

The sensing interlayer is sandwiched between individual split-ring resonators as shown in FIG. 3A. The device geometry can make the quality factor and resonant frequency of the antenna highly dependent on the interlayer, enhancing device performance in comparison to planar SRR-based dielectric sensors (FIG. 3B). The construct enables: (i) detection of changes in interlayer thickness, (ii) engineerable delays in antenna response through controllable transport properties of solutes into the interlayer, and (iii) increased sensitivity due to the concentration of the E-field within the interlayer.

Experimental Procedures

Substrate Preparation: Fabrication of trilayer structures on flexible substrates was accomplished using a sacrificial layer technique. Glass slides were cleaned in acetone, isopropanol, and oxygen plasma. A photoresist sacrificial layer was then spun and baked (spr-220, 3 μm) before e-beam deposition of Ti (30 nm)-Au (200 nm)-Ti (30 nm) as a seed layer. The photoresist was then coated and patterned to 7 μm (spr 220), the titanium overlayer was etched (1% HF), and gold was deposited via electroplating (Elevate Gold 7990, Technics). Gold was overplated to a thickness of 14 μm so as to create a mushroom structure. Seed layers were etched in titanium etchant (1% HF) followed by gold etchant (Transene), and then finished in titanium etchant. Silk fibroin (30 MB, prepared using established protocols) was dried onto substrates to form a thin 5 μm thick film and then water-annealed overnight in a high-humidity vacuum chamber. Water-soluble tape was then attached onto films to form a secondary substrate during release of silk film substrates of the carrier glass slide (with acetone). The general fabrication process is depicted in FIG. 3C, sections 1-4.

To form silk film interlayer structures, silk fibroin (30 MB, 8%) was spun onto substrates to form a thin film. Separate films were then aligned and embossed together using a custom embossing setup (100° C., 20 psi) to form a final, shelf stable structure composed of silk film-SRR trilayer flanked by water-soluble tape. Before studies, these structures were released from tape and pretreated over 24 hours in deionized water.

To form hydrogel-interlayer structures, film-SRR structures were released from water-soluble tape with water, and rescaffolded onto plastic coverslips (Fischer). For silk hydrogel, silk hydrogel solution (15 μL, composed of 6% fibroin mixed with 10 U mL$^{-1}$ of horseradish peroxidase and 0.01% hydrogen peroxide) was deposited above individual SRRs. The second half of the structure was then aligned and set above this first layer, and allowed to gel overnight. For PNIPAM hydrogel, NIPAM solution (composed of 10% NIPAM, 0.1% bis acrylamide, and 0.8% acrylic acid in DI) was combined with ammonium persulfate and TEMED to a final concentration of 0.8% APS and TEMED. 3 μL of solution was deposited between the SRR's. The solution was mixed at 0° C. to prevent premature gelation during mixing and allow rapid gelation when added to the room temp SRR's. Following gelation, the samples were placed in DI water overnight.

In Vitro Characterization: Resonant response of 3 mm by 3 mm antennas was characterized with a HP 8753E impedance analyzer using a small loop (3 mm) attached to the coaxial input. Interlayer structures were placed on a coverslip within a poly(dimethylsiloxane) (PDMS) stencil, and desired liquids were infiltrated within the stencil opening. A variety of liquids including deionized water, artificial saliva (Xialine 2 formulation), salty artificial saliva (200 mg $L^{-1}$), methanol, 50% ethanol, and various concentrations of salt and glucose in deionized water were tested.

In Vivo Characterization: For in vivo measurements, recently dried silk fibroin interlayer sensors were attached to one side of double-sided tape (3M), and covered with a perforated thin plastic sheet. The opposite end of the double-sided tape was then affixed to the dried tooth of human subjects. Sensors were then allowed to rewet with subject saliva over 15 min before data were collected. For detection of base sensor response to different solvents, subjects were told to swish respective liquids (tap water, apple juice, cup noodle soup, or mouthwash) for roughly 2 min before sensor response was collected. Resonant response of sensors was characterized with a miniVNA Tiny vector network analyzer. A small loop antenna (4 mm) with an attached 0.25 mm thick insulating plastic backing was used to gather data from the sensors. The plastic backing was gently placed on the resonator and the loop antenna was aligned to the sensor by eye before taking data.

Results

To confirm the usability of the device in biological environments, multiple devices were tested by immersion in saline solutions. The devices were found to maintain their format without visible delamination of the layers and a baseline operational frequency of $f_{resonance} \approx 400$ MHz was measured for a 3 mm by 3 mm device footprint. Devices down to 2 mm by 2 mm footprint were fabricated and showed a measurable resonant response.

To demonstrate the effectiveness of the interlayer as the functional element of the device, demonstrator trilayer constructs were assembled by including different materials between SRRs realized onto films of silk fibroin. Silk was used as the outer layer of the device for its biocompatibility, its ability to controllably absorb and swell to different thicknesses in a variety of solvents (including water and ethanol), and its ability to be penetrated by biomolecules. The transport properties of silk films can also be regulated via the control of the protein conformation in film format. Target demonstrations were explored by including interlayer materials that are responsive to analytes, temperature, or pH. Specifically, the materials encapsulated were a hygroscopic silk film, or hydrogel-based interlayers such as a silk gel or a responsive poly(N-isopropylacrylamide), PNIPAM-based hydrogel.

Eigenfrequency simulations in COMSOL (RF module) were used to verify the resonant response of the SRRs and BC-SRRs with varying dielectric thickness. The dependence of the BC-SRR response to the thickness of the interlayer is confirmed by the size of the fringing fields that are of the same order of magnitude as the interlayer thickness (FIG. 3B) as further illustrated by the relationship between the resonant frequency and the interlayer thickness (FIG. 3D).

Constructs with silk film interlayers were evaluated in vitro in response to solvents with varying degrees of ionic strength, glucose concentration, and solvent concentration. Sensor performance while immersed in deionized (DI) water was found to be in agreement with the simulations. Devices with thinner interlayer films ($\approx 1.2$ μm) exhibited lower resonant frequencies (300-450 MHz), while thicker interlayer films ($\approx 2.3$ μm) exhibited higher resonant frequencies (525-650 MHz) in DI water. Without being bound by theory, the sensor-to-sensor variation in resonant frequency ($\pm 100$ MHz) and amplitude ($-1$ to $-3$ dB) is attributed to the manufacturing protocol of the devices, namely: (i) the different offset in the orientation/alignment of split-rings to each other (any offset will increase the resonant frequency), and (ii) the uneven spin-coating of silk fibroin or uneven pressure distribution during trilayer sealing. These sensor-to-sensor variations affect the base resonant frequency which is measured in water prior to testing. Shifts from this base frequency are used to characterize the surrounding fluid. Due to these variations from fabrication, the sensors need to be calibrated in known solutions prior to performing measurements. It is expected that improvements in manufacturing would provide a consistent baseline and remove the need for this step.

To address simple examples of human food consumption, a single, thin-interlayer RF sensor was exposed to solutions including DI water, artificial saliva, 50% alcohol (ethanol), methanol, and high salinity saliva. Solution infiltration in the interlayers affects the response of the device by modulating its amplitude response and resonant frequency. Signals from the device were detected by using an RF network analyzer connected to a reading coil. Different analytes can be successfully discriminated as illustrated in FIG. 4B. In the signals detected, in comparison to deionized water, artificial saliva possessed a lower amplitude (and slightly lower resonant frequency) due to its higher ionic strength, while alcohol led to an increase in the resonant frequency due to a lower net permittivity. Finally, higher-salinity artificial saliva led to a large reduction in amplitude (and a small reduction in resonant frequency). In general, it was easier to discriminate separate solutions in sensors with thinner interlayers than thicker ones likely because of the sharper resonance of thinner film devices and the associated higher sensitivity as a function of changes in interlayer thickness. Additional tests were performed by dissolving glucose in the solution under analysis. Increasing concentration of glucose leads to an increasing resonant frequency response of the sensor as its presence reduces the effective permittivity of solutions (FIG. 4C). The corresponding temporal response of sensors to step-variations in glucose is was monitored. The trilayer displays sensitivities (in vitro) of around 0.6 MHz in 1 g $L^{-1}$ of glucose (FIG. 4C), well within the range required to detect sugar in drinks (e.g., fruit juice possesses up to 100 g $L^{-1}$ sugar).

Due to the transient nature of solutions in the mouth, it is often desirable for a sensor to measure the average content of its surroundings to avoid signal fluctuations as saliva continuously mixes with food or drink. In the constructs presented here, the interlayer provides a short-term reservoir that averages solution concentrations over time. This time window can be controlled by the rate of solution penetration into the layer through the control of transport through the outer layers of the device. The response rates of thin ($\approx 1.2$ μm) and thick ($\approx 2.3$ μm) interlayer sensors from deionized water to 50% ethanol were tested. Thicker films exhibited slightly faster response rates than thinner films, which is likely due to faster diffusion rates of solvents into the thicker interlayers. The general temporal response of trilayer sensors ($\approx 2.3$ μm thick) to infiltration and release of high-salt and high-alcohol solutions are shown in FIGS. 4E-F. Interestingly, we found infiltration and release rates to be negatively correlated. Exposure to high-salinity solutions rapidly reduced the signal amplitude, however the amplitude was slow to recover. The inverse was true for high-alcohol solutions, which exhibited lower penetration times yet faster reset times. These results are likely due to properties of the interlayer as silk possesses a relatively large net negative charge at physiological pH (to facilitate penetration of sodium ions), and is hygroscopic (with a slight preference for absorption of water over other solvents).

Interlayers composed of hydrogels were then examined by first using a soft (<10 kPa), ≈40 μm thick silk hydrogel as the interlayer due to the adhesive properties of silk hydrogel to silk film and metals. Despite the differences in the respective thickness of hydrogel and film interlayers, sensors display similar resonant frequencies (≈400 MHz to 1 GHz). This is likely due to the higher effective permittivity of hydrogel interlayers due to water content. pH and temperature-sensitive interlayers can be achieved by using responsive PNIPAM hydrogels. These sensors experience a large frequency shift due to volume phase transitions of the hydrogel induced by temperature or pH that cause a thickness change of the layer. This response dominates over the decrease in permittivity that occurs due to this transition. These gels exhibited poor adhesion properties when compared to the silk hydrogels, and thus required vapor pre-deposition of 3-methacryloxypropyltrimethoxysilane to facilitate covalent bonding between the titanium and hydrogel acrylate groups. Similar to previously described cases, we found variation in the base resonant frequency from sensor to sensor, this time mainly due to fluctuations in the gel thickness in the interlayer. The initial response of the PNIPAM loaded devices to varying temperatures is shown in FIG. 5C. PNIPAM hydrogels collapse in size at around 35° C., and this response was evident from temperature ramping (FIG. 5C) and temperature relaxation. Sensor response remained consistent across multiple iterations with no noticeable change to the appearance of fabricated structures (FIG. 5E). A second PNIPAM hydrogel-interlayer sensor was tested under changing pH (with constant ionic strength). Its resonant frequency dropped over 50 MHz upon exposure to a pH shift of 5 to 3 (FIG. 5D). Similar to controlled changes in temperature, exposure of trilayer sensors to a changing pH leads to repeatable shifts in its resonant frequency (FIG. 5F). For both temperature and pH, use of a responsive hydrogel enables discrimination between pH or temperature around a threshold determined by the properties of the hydrogel.

The functionality of silk-film trilayer sensors was evaluated for in vivo sensing of common liquid environments in the human mouth (FIG. 6A). The study included measurements in dry-mouth conditions and following consumption of tap water, apple juice, alcohol, mouthwash, and soup. In total, four separate tests were performed on human subjects in accordance to approved institutional protocols. Three of the tests used thinner (≈1 μm) interlayers, while one trial tested an ≈2.3 μm thick interlayer. FIG. 6B shows a representative trial result. The response of the trilayer devices was measured by using a mobile reader, composed of a portable vector network analyzer (VNA) attached to a tablet or cell phone. The in vivo measurements exhibit similar trends to the in vitro measurements with shifts in resonant frequency and amplitude as a function of the different solvents, ionic strength, and presence of sugar. Consistent with previous measurements it was easier to discriminate liquids with structures that had thinner interlayers. Preliminary in vivo studies on the responses/recovery time of sensors after exposure to soup (i.e., high salt), mouthwash, and drying were studied.

Finally, to assess the repeatability and stability of the sensor response to different, varying solutions, data from the sensors were taken over a period of a week with repeated changes between DI, PBS, and glucose (0.5 g $L^{-1}$) (FIGS. 6C-D). These data show that residual solute upon solution change is negligible with no appreciable shift in the baseline sensor response over time. The broadside coupled multilayer antenna format combined with biopolymer-based permeable membranes and biologically active sensing layers provides an approach for a compact conformal platform for convenient sampling and sensing of analytes and sensing of foods and liquid consumption.

By using interlayers composed of biopolymer films or responsive hydrogels, these constructs can be mounted directly onto human tooth enamel and become sensitized to a wide variety of fluid properties such as alcohol content, salinity, sugars, pH, temperature, with the opportunity of adding more specifically functionalized layers for targeted sensing. The few millimeter physical footprint makes these functional constructs convenient and adaptable to a variety of environments extending the applicability of RF sensors and allowing distributed, multiplexed sensing with the integration of additional responsive interlayers.

In conclusion, novel systems and methods for detecting physiological variables within the oral cavity of a subject are provided. In one aspect, the sensors are sized and designed to fit onto a single human tooth to sample biofluids in the oral cavity and discriminate between physiological parameters, such as the concentration of consumed foods or liquids. The favorable functionality and reduced form factor of the dielectric sensor may be achieved through the use of a split-ring resonator and unique material selections.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed:

1. A dielectric sensor configured to detect a physiological variable within a subject, the dielectric sensor comprising: a split-ring resonator configured to be positioned within an oral cavity of the subject and to be bioresponsive to at least one physiological variable, the split-ring resonator comprising:
    a first resonator loop;
    a second resonator loop; and
    a dielectric interlayer interposed between and contacting the first resonator and the second resonator, wherein the dielectric interlayer comprises a material selected from the group consisting of a silk film, a silk gel, a responsive poly(N-isopropylacrylamide) hydrogel, a PNIPAM-based hydrogel, and combinations thereof.

2. The dielectric sensor of claim 1, wherein the dielectric interlayer has a thickness between the first resonator loop and the second resonator loop is between 0.5 and 3 micrometers.

3. The dielectric sensor of claim 1, wherein the first resonator loop and the second resonator loop are positioned to form a broadside-coupled split-ring resonator.

4. The dielectric sensor of claim 1, wherein the physiological variable is selected from the group consisting of glucose concentration, ethanol concentration, salinity, pH, and temperature.

5. The dielectric sensor of claim 1, wherein the dielectric sensor is sized to fit within a 3 mm by 3 mm by 1 mm box.

6. The dielectric sensor of claim 1, wherein the dielectric sensor is configured to integrate with a tooth of the subject.

7. The dielectric sensor of claim 1 further comprising a porous outer layer enveloping the at least one split-ring resonator.

8. The dielectric sensor of claim 7, wherein the porous outer layer comprises silk fibroin.

9. The dielectric sensor of claim 1, wherein the dielectric interlayer undergoes a change in thickness as a bioresponse to the at least one physiological variable.

10. The dielectric sensor of claim 1, wherein the dielectric constant of the dielectric interlayer undergoes a change as a bioresponse to the at least one physiological variable.

11. A bio-sensing system configured to detect a physiological variable within a subject, the bio-sensing system comprising: a split-ring resonator configured to be positioned within an oral cavity of the subject and to be bioresponsive to at least one physiological variable, the split-ring resonator comprising:
   a first resonator loop;
   a second resonator loop;
   a dielectric interlayer interposed between and contacting the first resonator and the second resonator, wherein the dielectric interlayer comprises a material selected from the group consisting of a silk film, a silk gel, a responsive poly(N-isopropylacrylamide) hydrogel, a PNIPAM-based hydrogel, and combinations thereof; and
   a radiofrequency (RF) network analyzer configured to detect the resonant frequency and amplitude generated by the split-ring resonator; and
   a processing system coupled to the RF network analyzer configured to:
      control the RF network analyzer to detect the resonant frequency and amplitude generated by the at least one split-ring resonator; and
      provide information regarding the at least one physiological variable.

12. The bio-sensing system of claim 11 further comprising at least one additional split-ring resonator configured to be positioned within an oral cavity of the subject and to be bioresponsive to at least one additional physiological variable.

13. The bio-sensing system of claim 11, wherein the first resonator loop and the second resonator loop are positioned to form a broadside-coupled split-ring resonator.

14. The bio-sensing system of claim 11, wherein the physiological variable is selected from the group consisting of glucose concentration, ethanol concentration, salinity, pH, and temperatures.

15. The bio-sensing system of claim 11, wherein the at least one split-ring resonator is configured to integrate with a tooth of the subject.

16. The bio-sensing system of claim 11, wherein the dielectric interlayer undergoes a change in thickness as a bioresponse to the at least one physiological variable, thereby altering at least one of the resonant frequency or resonant amplitude of the generated by the at least one split-ring resonator.

17. The bio-sensing system of claim 11, wherein the dielectric constant of the dielectric interlayer undergoes a change as a bioresponse to the at least one physiological variable, thereby altering at least one of the resonant frequency or resonant amplitude of the generated by the at least one split-ring resonator.

18. A method of detecting a physiological variable within a subject, the method comprising:
   positioning a dielectric sensor within an oral cavity of the subject, wherein the dielectric sensor comprises at least one split-ring resonator configured to be bioresponsive to at least one physiological variable, the split-ring resonator comprising:
      a first resonator loop;
      a second resonator loop; and
      a dielectric interlayer interposed between and contacting the first resonator and the second resonator, wherein the dielectric interlayer comprises a material selected from the group consisting of a silk film, a silk gel, a responsive poly(N-isopropylacrylamide) hydrogel, a PNIPAM-based hydrogel, and combinations thereof;
   applying a controlled electromagnetic field to the dielectric sensor;
   detecting the resonant frequency and amplitude generated by the dielectric sensor; and
   providing information regarding the at least one physiological variable.

* * * * *